United States Patent [19]

Monson

[11] Patent Number: 4,863,477
[45] Date of Patent: Sep. 5, 1989

[54] SYNTHETIC INTERVERTEBRAL DISC PROSTHESIS

[76] Inventor: Gary L. Monson, 631-15th St. E.-#202, West Fargo, N. Dak. 58078

[21] Appl. No.: 51,230

[22] Filed: May 12, 1987

[51] Int. Cl.$^4$ .............................................. A61F 2/44
[52] U.S. Cl. .................. 623/17; 128/924 M
[58] Field of Search .................. 623/11, 12, 13, 17; 128/924 M

[56] References Cited

U.S. PATENT DOCUMENTS

| | | | |
|---|---|---|---|
| 3,768,102 | 10/1973 | Kwan-Gett et al. | 623/11 |
| 3,875,595 | 4/1975 | Froning | 623/17 |
| 4,349,921 | 9/1982 | Kuntz | 623/17 |
| 4,531,244 | 7/1985 | Hamas | 623/8 |

Primary Examiner—Richard J. Apley
Assistant Examiner—David Isabella
Attorney, Agent, or Firm—Berman, Aisenberg & Platt

[57] ABSTRACT

A synthetic intervertebral disc prosthesis, molded in the same shape and general dimensions as a natural disc which it replaces after removal of a damaged natural disc, is molded of a biologically acceptable, non-porous, preferably rubber or silicone-rubber compound in two halves, each half having a hollow, molded interior. The two halves are joined together with a non-toxic adhesive to form a body having a fluid-tight cavity in its interior. The upper and lower surfaces of the disc each have a plurality of small suction cup-like projections molded thereon for frictionally engaging adjacent vertebrae. After the two halves of the prosthesis are joined, the prosthesis is implanted between two vertebrae in place of a removed natural disc, and a volume of fluid, such as saline solution, is injected into the interior cavity of the prosthesis to create the necessary amount of resilliency which restores proper vertebral spacing and facilitates flexibility of the spinal column.

18 Claims, 1 Drawing Sheet

U.S. Patent     Sep. 5, 1989     4,863,477
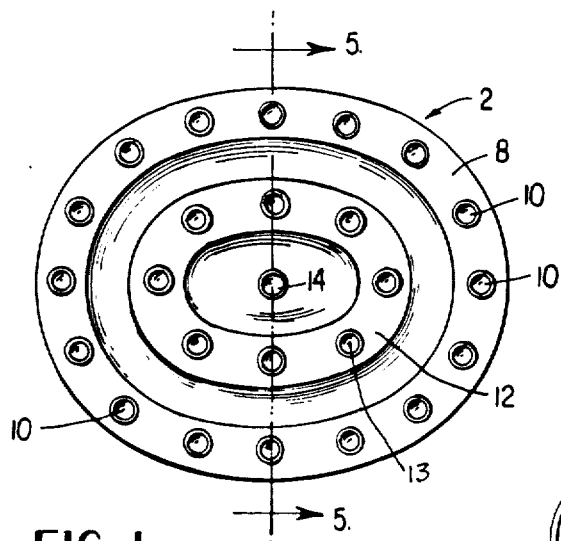
FIG. 1
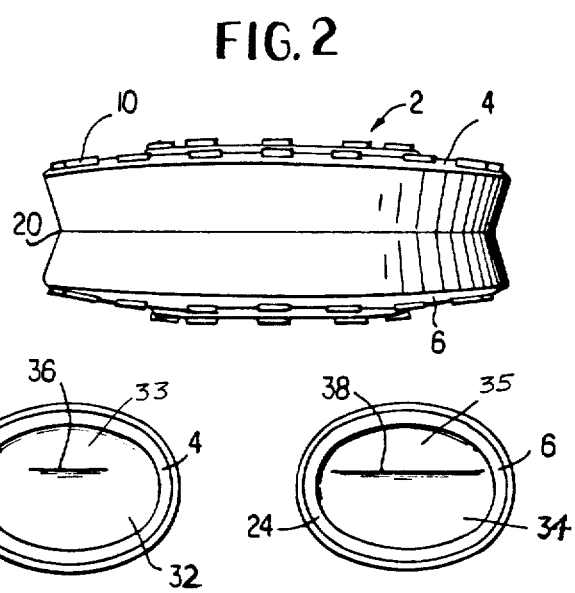
FIG. 2
FIG. 3     FIG. 4
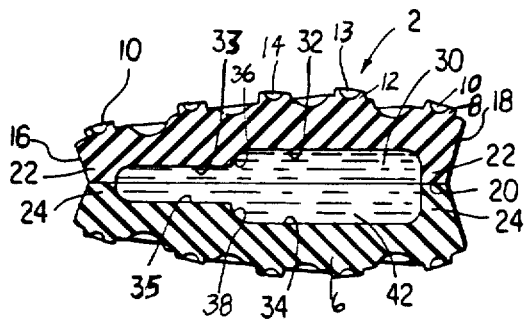
FIG. 5
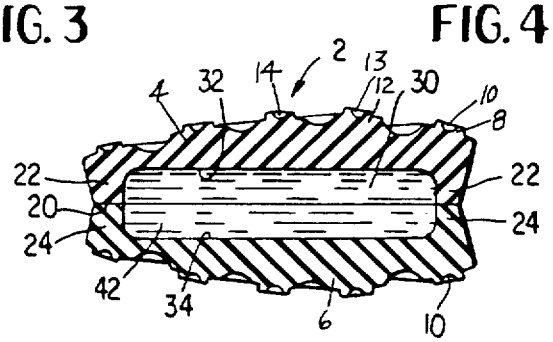
FIG. 6
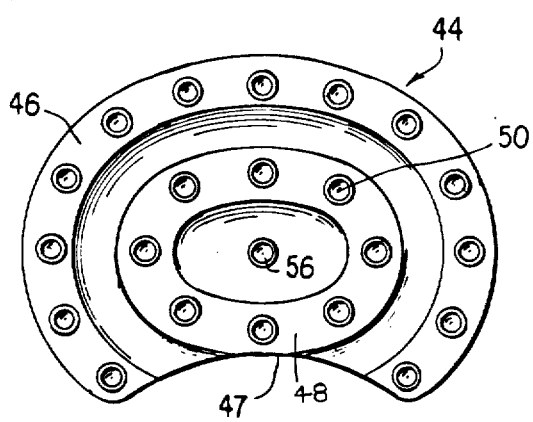
FIG. 7
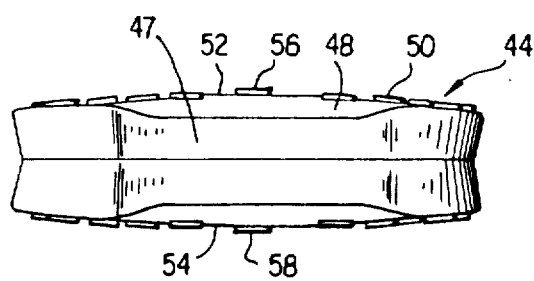
FIG. 8

SYNTHETIC INTERVERTEBRAL DISC PROSTHESIS

FIELD OF THE INVENTION

The invention relates to a synthetic intervertebral disc prosthesis for insertion into a spine in place of a removed natural disc.

BACKGROUND OF THE INVENTION

In cases of spinal injury, surgery to remove an intervertebral disc in the spinal column may be necessary. The vertebrae of the spinal column are connected together by intervertebral fibrocartilaginous discs. The discs maintain a separation between the vertebrae, but are sometimes damaged and/or become narrowed so that the intervertebral separation is reduced. This produces pain, and in order to alleviate the symptoms resulting from this intervertebral disc failure, a disc may need to be removed.

When a disc has been removed, the vertebrae may be fused together, resulting in complete loss of flexibility of the spinal column at this location, or the damaged disc may be replaced with a disc prosthesis intended to duplicate the function of the natural spinal disc. Many such spinal disc prostheses have been proposed, but none are completely satisfactory.

The patent to Kuntz, U.S. Pat. No. 4,349,921 describes an intervertebral disc prosthesis comprising a body of biologically-acceptable material suitably dimensioned and shaped to replace a natural disc. One end of the prosthesis has a raised flange to prevent penetration of the disc prosthesis to an excessive depth into the spinal joint. The prosthesis is made up of several laminar sections, placed vertically. This device, having its parts located in side-by-side relationship does not give the spine sufficient flexibility. The patent to Froning, U.S. Pat. No. 3,875,595, shows a collapsible plastic bladder-like prosthesis, for filling with liquid. The top and bottom surfaces of the synthetic disc have stud-like protrusions which fit into sockets fastened into the adjacent vertebrae. The device is complex, and requires physical attachment to the adjacent vertebrae.

The patent to Stubstad, U.S. Pat. No. 3,867,728, shows a shaped spinal prosthesis having a top covering and a bottom covering which are secured together using textile fabric. The Patil patent, U.S. Pat. No. 4,309,777 describes an artificial intervertebral disc for implantation in the disc space after removal of a damaged disc. The Patil disc has a plurality of springs positioned between top and bottom surfaces to provide flexible movement of the vertebrae. The intervertebral disc of Patil is secured with a plurality of spikes extending upward and downward from the prosthesis, anchoring the disc to the vertebrae.

SUMMARY OF THE INVENTION

A synthetic intervertebral disc prosthesis, molded in the same shape and general dimensions as a natural disc which it replaces after removal of a damaged natural disc is molded of a biologically acceptable, non-porous, preferably rubber or silicone-rubber compound in two halves, each half having a hollow, molded interior. The two halves are joined together with a non-toxic adhesive to form a body having a fluid-tight cavity in its interior. The upper and lower surfaces of the disc prosthesis each have a plurality of small suction cup-like projections molded thereon for frictionally engaging adjacent vertebrae. After the two halves of the prosthesis are joined, the prosthesis is implanted between two adjacent vertebrae in place of a removed natural disc, and a volume of fluid, such as saline solution, is injected into the interior cavity of the disc prosthesis to create the necessary amount of resiliency which restores normal vertebral spacing and facilitates flexibility of the spinal column.

It is an object of the invention to provide an improved spinal disc prosthesis.

It is a further object of the invention to provide a method for using the spinal disc prosthesis of the invention.

BRIEF DESCRIPTION OF THE DRAWINGS

FIG. 1 is a top plan view of a synthetic disc prosthesis of the invention.

FIG. 2 is a side elevation view of the device of FIG. 1.

FIG. 3 is a top plan view of the inside of the top part of the prosthesis of FIG. 1.

FIG. 4 is a top plan view of the inside of the bottom part of the prosthesis of FIG. 1.

FIG. 5 is a cross-sectional view taken on line 5—5 of FIG. 1.

FIG. 6 is a cross-sectional view of an alternative embodiment of FIG. 1.

FIG. 7 is a top plan view of another embodiment of the invention of FIG. 1.

FIG. 8 is a side elevational view of the spinal prosthesis of FIG. 7.

DETAILED DESCRIPTION OF THE INVENTION

An intervertebral disc prosthesis of the invention is a synthetic disc molded of approximately the same size and shape as a natural disc which it replaces after a diskectomy. The synthetic disc is molded of a biologically compatible, non-porous rubber, silicone-rubber or synthetic plastic material each half having a hollow, molded interior which, when joined together with a non-toxic adhesive, form a body having a fluid-tight cavity. After implantation of the synthetic disc between two vertebrae, a volume of fluid, such as saline solution is injected into the synthetic disc to create necessary resiliency and restore the original vertebral spacing, as well as facilitating flexibility of the spine.

In the lumbar region of the spine of a human adult, a natural disc has an approximate thickness of from 8 to 13 mm., depending upon overall body size, with a difference in thickness of about 2 mm. between its anterior and posterior edges. A synthetic disc is about the same size and general shape as the natural disc it replaces. The top and bottom of the synthetic disc are each preferably slightly convex in shape, both laterally and longitudinally, and have gripping means, preferably (a plurality of molded raised protrusions. The raised protrusions are, for example, tiny suction cups. The tiny suction cups provide frictional adhesion of the outer surfaces to the slightly concave adjacent surfaces of the adjacent vertebrae and prevent dislocation of the prosthesis once implantation is completed. The suction cups are typically located on one or more concentric rings or other closed figure configuration molded into the outer surface of the top and/or bottom of the disc. Two or more concentric rings may also be used. In a typical example, a disc prosthesis has an outer ring, of about 5 mm. in width and an inner ring of about 4 mm. in width on the surface of the top and/or bottom of the synthetic disc, on which the molded suction cups are positioned. The suction cups may alternatively be positioned directly on the top surface and/or bottom surface of the prosthesis, or may be positioned on molded raised portions of other configurations, such as lines, curves, spots, etc.

With reference to FIGS. 1 to 8, in which like numerals represent like parts, FIG. 1 sows a typical synthetic spinal disc 2 of the invention. Synthetic disc 2 is of generally oval shape and has a slightly convex shape to its top surface 4 and bottom surface 6, as clearly shown in FIG. 2. Synthetic disc 2 is of generally oval shape and has a ring 8 around its perimeter on which a plurality of small suction cup-like projections 10 are situated. Inner ring 12 likewise has suction cups 13 positioned thereupon. FIG. 1 shows suction cup 14 in the center of the surface of disc 2, and suction cup 14 may be elevated on a molding as shown in FIGS. 5 and 6.

The rings and suction cup-like projections are spaced appropriately for providing frictional engagement with the adjacent vertebral surfaces, and the outermost ring either may be spaced adjacent to, or may be spaced away from, the outer perimeter of the synthetic disc. Alternatively, only one ring or three or more rings may be present, or the suction cups (or other frictional gripping means) may be arranged otherwise than on rings. The number and spacing of the gripping means is not critical, but an adequate number are needed. Suction cups provide particularly good frictional engagement of the disc to the lower surface of the vertebra adjacent the top surface of the disc or to the upper surface of the vertebra adjacent the bottom surface of the disc. Disc 2 is made from rubber, silicone-rubber or other suitable rubber and/or synthetic plastic resilient material known to one skilled in the art. FIG. 5 illustrates that the height of the back edge 16 is less than the height of the front edge 18 of the synthetic disc, as in a natural spinal disc.

Synthetic disc 2 is molded in two similar halves 4 and 6 joined along adjacent edges at 20. The two halves of the synthetic disc may be joined by any compatible adhesive known to one skilled in the art. Each half 4, 6 of the synthetic disc has a lip or wall 22, 24 respectively, shown in FIGS. 3 and 4, molded around the edge. Each edge wall 22, 24 is joined to the edge wall of the other half of the synthetic disc when the unit is assembled. As shown in FIGS. 5 and 6, edge wall 22 of top half 4 joins edge wall 24 of bottom half 6 to form a complete synthetic disc 2. Inside the walls 22, 24 either a substantially flat inner surface 32, 34 is present on the inside of top 4 and bottom 6 of synthetic disc 2, as shown in FIG. 6, or a ridge 36, 38 may be present on each inner surface, as shown in FIGS. 3 to 5. Ridge 36 in top surface 32, together with ridge 38 in bottom surface 34, form a constricted area at the back of the synthetic disc. Ridges 36, 38 do not extend completely from end to end of the disc (as shown in FIGS. 3 and 4), to allow fluid to flow around the ends of the ridges. Ridge 36 in top half 4 typically extends further toward edge wall 22 of top half 4 than ridge 38 extends toward edge wall 24 of bottom half 6. As shown in FIGS. 3 and 4, both ridges are spaced in the interior of the two halves and do not touch edge walls 22, 24 of the synthetic disc. Ridges 36 and 38 channel the flow of a fluid 42, such as a saline solution, which is injected into the center of the disc after the disc has been inserted in the spinal column.

Ridges 36, 38 are pressure ridges which create a different interior floor height toward the rear of the synthetic disc. Ridges 36, 38 cause the floor 32, 34 of each half of the synthetic disc to slope upwards to a higher level 33, 35 at the back edge of each half causing a decrease in volume of interior fluid in the back half of the disc. This decrease in volume causes an increase in the pressure brought to bear along the crease of the mated disc halves, which in turn causes this crease to expand posteriorally as the spinal vertebrae arch to the rear. This same action takes place laterally and anteriorally when the body and spine bend from side to side or forward. Pressure ridges 36, 38 may be of differing width in each half of the disc and may be slightly domed to conform to the similarly domed, convex outer surfaces of the disc.

Since ridge 36, in the top half of the synthetic disc, is generally longer, and therefore larger, than ridge 38, in the bottom half of the disc, channels are formed at the outer edges of ridge 38, providing pressure relief channels for the fluid (such as saline solution) along the posterior wall after a shock to the spinal vertebrae has been absorbed. These channels allow the fluid to circulate back to the center of the cavity without obstruction. In this way, excessive buildup inside the synthetic disc is avoided if the body is subjected to a sudden backward arching motion. If the ridges were the same length, and if channels to provide pressure release were not present, ridges 36, 38 would collapse upon each other since no internal fluid would be able to migrate to the posterior portion of the disc prosthesis to provide flexibility. Other internal configurations providing channels for fluid flow will be apparent to one skilled in the art.

FIG. 7 shows another embodiment 44 of a synthetic spinal disc. The top and bottom surfaces of synthetic disc 44 are substantially "kidney" shaped, and the outside ring 46 is incomplete at back 47 of synthetic disc 44. FIG. 8 shows a rear elevation of synthetic disc 44 in which the concave upper surface formed by inner ring 48 of suction cups 50 forms a convex upper surface 52 and lower surface 54 for positioning adjacent the vertebra to replace a removed natural disc. Center suction cups 56, 58 may alternatively be the site of a more domed area on the inside of each half of the disc.

The synthetic disc of the invention may be a replacement for a removed natural lumbar disc, thoracic disc or cervical disc. A synthetic lumbar disc is shown in FIGS. 1 to 8. Thoracic and cervical discs are shaped appropriately, using the same principles as for the lumbar disc of FIGS. 1 to 8, having size and shape similar to natural thoracic and cervical discs, as known to one skilled in the art.

When the synthetic disc is prepared for use, the two halves are sealed together and air contained within the fluid-tight cavity is removed by aspiration. The disc is stretched longitudinally, and rolled into a cylindrical shape having the approximate diameter of a pencil or cigarette. The rolled disc is inserted into a plastic cylindrical container of the same approximate diameter and about 4 in. in length.

More specifically, deflation of the disc is accomplished by insertion of a small hypodermic needle into one of the posterior curves of the disc, and application of suction. The disc collapses as the air is aspirated, the evacuating needle is withdrawn and the compound of the disc self-seals, preventing reinflation of the disc. After deflation, the disc is fed into a winding mechanism comprising a slowly rotating slotted shaft, open on one end, which winds the disc into a cylindrical shape. On completion of winding, an ejection bar pushes the wound disc out and automatically removes it from the open end of the shaft. Simultaneously, the disc is washed with a saline solution emitted from a small nozzle and, as the disc slides from the shaft, it is inserted directly into a plastic cylindrical container. A plastic cap is placed over one end of this cylindrical container and the container is fed into a machine in which a pre-measured volume of saline solution is added to the cylinder around the disc. The remaining open end of the cylinder is closed, providing a "wet pack" for the disc which prevents the disc from adhering to itself during sterilization procedures or during storage.

Synthetic discs are made in various dimensions appropriate for insertion into various sizes of spine. A set containing several differently sized discs prosthesis is assembled and boxed, ready for sterilization. An appropriately sized disc prosthesis can readily be selected by measurement from X-rays, catscan images, etc. Each synthetic disc in the set is accompanied by an ejection plunger, slightly smaller in diameter and at least 1 in. longer than the cylinder, which facilitates removal of the disc from the cylinder during surgery. For implantation in the spine, an entire set of synthetic discs may be sterilized before surgery to provide the surgeon with a choice of discs if the pre-chosen disc should prove to be of unsuitable size.

At the point of implantation, following excision and removal of a damaged natural disc and its surrounding annulus, an ejection plunger is inserted into one end of the cylinder containing the synthetic disc selected for use, and the synthetic disc is moved to the end of the tube so that its end protrudes therefrom. A length of surgical thread is inserted (using a suture needle) through one of the posterior curved side shoulders of the disc, and the thread is pulled out to an equal double length. The ejection plunger is retained in the cylinder against the rolled disc. When the point of insertion is determined and an adequate space is secured by means of retracting clamps on the surfaces of the two opposing vertebrae, the dual surgical threads are inserted through the space vacated by the excised natural disc and drawn out by forceps, so that the surgeon has the dual threads in one hand and the disc cylinder in the other hand. The surgeon brings the cylinder with the end of the synthetic disc protruding therefrom up to the hole in the vertebral bone (probably 10 mm. or less) and as the end of the cylinder contacts that opening, the ejection plunger is pushed against the rolled up disc, and the disc is ejected from the tube as the surgeon pulls the dual threads, drawing the disc into the interior cavity between the two vertebrae. The packaging cylinder and ejection plunger are then discarded. The synthetic disc is unrolled using an appropriate implement, enabling it to occupy the entire vacant cavity between the vertebrae in place of the natural disc and annulus. The synthetic disc, in a flattened configuration between the vertebrae, is injected with a fluid, such as saline solution, which inflates the disc to a convex configuration.

A hypodermic needle is inserted in the crease of the synthetic disc, typically at the posterior curve and at about a 25° angle to the disc, so as to puncture the interior cavity at an angle. A suitable volume of fluid, such as 0.9% (or less) saline solution or other non-toxic fluid, is injected through the wall of the disc into the cavity. About 2 cc. of fluid may be used according to the size of disc. The edge wall of the disc is about 4–5 mm. in thickness. The needle is withdrawn at the same as it was inserted, and the disc seals itself, preventing leakage of fluid under the stress of compression. Other suitable fluids will be known to one skilled in the art. The dual threads in the disc shoulder are withdrawn and implantation is complete. The retraction clamps are removed after checking the disc for correct alignment with the upper and lower vertebral surfaces.

Other surgical techniques for disc implantation will be apparent to one skilled in the art. The procedure outlined above is described for insertion posteriorally. Lumbar diskectomy may alternatively be performed retroperitoneally or anteriorally. The synthetic disc described herein may also be used with either of these techniques. For an anterior approach, the synthetic disc does not require the packaging described and may be packaged in its oval, deflated form and inserted in this flattened state directly into the vertebral cavity after excision of the natural disc and surrounding annulus.

The synthetic disc is inexpensive to manufacture and not likely to cause allergic reaction in the patient. Properly implanted, the synthetic disc should require no further attention during the patient's lifetime.

While the invention has been described above with respect to certain embodiments thereof, it will be appreciated that variations and modifications may be made without departing from the spirit and scope of the invention.

What is claimed is:

1. A synthetic intervertebral disc prosthesis of flexible, non-porous, biologically compatible material, for replacing a natural intervertebral disc, comprising:

a substantially oval disc of about the same size and shape as the natural intervertebral disc which it replaces, including a convex upper surface for non-invasively abutting a lower surface of a first vertebra, a convex lower surface for non-invasively abutting an upper surface of a second vertebra located adjacent and below said first vertebra, a fluid-tight cavity between said upper surface and said lower surface of the prosthesis, and gripping means for frictionally engaging at least one of said lower surface of the first vertebra and upper surface of the second vertebra, said gripping means being situated on at least one of the upper surface and the lower surface of the prosthesis, said gripping means including at least one raised protrusion providing frictional adhesion to the adjacent vertebra surface, wherein at least a portion of said gripping means is positioned in a substantially closed ring configuration on at least one of the upper surface and lower surface of the prosthesis.

2. A prosthesis of claim 1 wherein the gripping means comprises one suction cup.

3. A prosthesis of claim 2 wherein the gripping means comprises a plurality of suction cups.

4. A synthetic intervertebral disc prosthesis of flexible, non-porous, biologically compatible material, for replacing a natural intervertebral disc, comprising:

a substantially oval disc of about the same size and shape as the natural intervertebral disc which it replaces, including a convex upper surface for abutting a lower surface of a first vertebra, a convex lower surface for abutting an upper surface of a second vertebra located adjacent and below said first vertebra, a fluid-tight cavity between said upper surface and said lower surface of the prosthesis and gripping means for frictionally engaging at least one of said lower surface of the first vertebra and upper surface of the second vertebra, said gripping means being situated on at least one of the upper surface and the lower surface of the prosthesis, said gripping means including at least one raised protrusion providing frictional adhesion to the adjacent vertebra surface, wherein at least a portion of said gripping means is positioned in a substantially closed ring configuration on at least one of the upper surface and lower surface of the prosthesis, and at least one of said gripping means on at least one of the upper surface or lower surface of the prosthesis further comprises a plurality of suction cups.

5. A prosthesis of claim 1 made of flexible, compressible material.

6. A prosthesis of claim 5 wherein the material is a member selected from the group consisting of rubber, silicone-rubber compounds, plastic material and a combination of rubber and plastic material.

7. A prosthesis of claim 1 wherein fluid is contained in the cavity.

8. A prosthesis of claim 7 wherein the fluid is saline solution.

9. A prosthesis of claim 1 wherein the upper surface and lower surface of the prosthesis comprise separate pieces each having outer and inner surfaces such that when joined together respective inner surfaces form an interior cavity of the prosthesis.

10. A prosthesis of claim 9 wherein said cavity is filled with a fluid and at least one of said inner surfaces comprises means upstanding therefrom for directing flow of said fluid.

11. A prosthesis of claim 10 wherein both of said inner surfaces means upstanding therefrom comprise means for directing the flow of said fluid.

12. A prosthesis of claim 9 wherein the separate pieces are substantially identically formed.

13. A prosthesis of claim 1 wherein said upper surface and said lower surface are joined by a perimeter wall.

14. A synthetic intervertebral disc prosthesis of flexible, non-porous, biologically compatible materials, for replacing a natural intervertebral disc, comprising:
a substantially oval disc of about the same size and shape as the natural intervertebral disc which it replaces, including a convex upper surface for non-invasively abutting a lower surface of a first vertebra, a convex lower surface for non-invasively abutting an upper surface of a second vertebra located adjacent and below said first vertebra, a fluid-tight cavity between said upper surface and said lower surface, and gripping means for frictionally engaging at least one of said lower surface of the first vertebra and upper surface of the second vertebra, said gripping means being situated on at least one of the upper surface and the lower surface of the prosthesis, said gripping means including at least one raised protrusion providing frictional adhesion to the adjacent vertebra surface, wherein at least a portion of said raised protrusion is positioned in a substantially closed ring configuration on at least one of the upper surface and the lower surface of the prosthesis.

15. A synthetic intervertebral disc prosthesis of flexible, non-porous, biologically compatible materials, for replacing a natural intervertebral disc, comprising:
a substantially oval disc of about the same size and shape as the natural intervertebral disc which it replaces, including a convex upper surface for abutting a lower surface of a first vertebra, a convex lower surface for abutting an upper surface of a second vertebra located adjacent and below said first vertebra, a fluid-tight cavity between said upper surface and said lower surface, and gripping means for frictionally engaging at least one of said lower surface of the first vertebra and upper surface of the second vertebra, said gripping means being situated on at least one of the upper surface and the lower surface of the prosthesis, said gripping means including at least one raised protrusion providing frictional adhesion to the adjacent vertebra surface, wherein at least a portion of said raised protrusion is positioned in a substantially closed ring configuration on at least one of the upper surface and the lower surface of the prosthesis, and wherein at least a portion of said protrusion further comprises a plurality of suction cups positioned thereon.

16. A synthetic intervertebral disc prosthesis of flexible, non-porous, biologically compatible material, for replacing a natural intervertebral disc, comprising:
an upper surface for abutting a lower surface of a first vertebra, a lower surface for abutting an upper surface of a second vertebra located adjacent and below said first vertebra, a fluid-tight cavity between said upper surface and said lower surface, and gripping means on said upper surface and said lower surface including at least one suction cup for frictional adhesion to at least one of said lower surface of the first vertebra and upper surface of the second vertebra, wherein the gripping means comprises a plurality of suction cups positioned in a ring configuration.

17. A prosthesis of claim 16 wherein the gripping means comprises a plurality of suction cups positioned on both said upper surface and said lower surface.

18. A method for implanting a synthetic intervertebral disc prosthesis in a spine in place of a removed natural disc between two adjacent vertebrae comprising:
removing air from within a fluid-tight cavity of a substantially oval disc prosthesis of about the same size and shape as the natural disc which it replaces, said prosthesis comprising a convex upper surface for abutting a lower surface of a first vertebra, a convex lower surface for abutting an upper surface of a second vertebra located adjacent and below said first vertebra, a fluid-tight cavity between said upper surface and said lower surface of the prosthesis, and gripping means for frictionally engaging at least one of said lower surface of the first vertebra and upper surface of the second vertebra, said gripping means being situated on at least one of the upper surface and the lower surface of the prosthesis, said gripping means including at least one suction cup providing frictional adhesion to the adjacent vertebra surface, inserting a prosthesis into a cylindrical container, ejecting a prosthesis from the container into a space between the two adjacent vertebrae, positioning the prosthesis with its convex upper and lower surfaces in abutting position between adjacent bone surfaces of said two adjacent vertebrae, without invading said bone surfaces, and injecting a fluid into the fluid-tight cavity to inflate the prosthesis and restore normal vertebral spacing in the spine.

* * * * *